(12) United States Patent
Gan et al.

(10) Patent No.: US 9,250,182 B2
(45) Date of Patent: Feb. 2, 2016

(54) IMAGING APPARATUS AND METHOD

(75) Inventors: Tat Hean Gan, Taiping Perak (MY);
David Arthur Hutchins, Coventry (GB); Geoffrey Graham Diamond, Coventry (GB)

(73) Assignee: The University of Warwick, Coventry (GB)

( * ) Notice: Subject to any disclaimer, the term of this patent is extended or adjusted under 35 U.S.C. 154(b) by 1042 days.

(21) Appl. No.: 12/306,505

(22) PCT Filed: Jun. 28, 2007

(86) PCT No.: PCT/GB2007/050368
§ 371 (c)(1),
(2), (4) Date: Dec. 23, 2008

(87) PCT Pub. No.: WO2008/001141
PCT Pub. Date: Jan. 3, 2008

(65) Prior Publication Data
US 2009/0279773 A1 Nov. 12, 2009

(30) Foreign Application Priority Data
Jun. 28, 2006 (GB) .................................. 0613165.0

(51) Int. Cl.
*G06K 9/00* (2006.01)
*G01N 21/59* (2006.01)
(Continued)

(52) U.S. Cl.
CPC .............. *G01N 21/59* (2013.01); *A61B 5/0059* (2013.01); *G01N 21/4795* (2013.01); *G01N 21/55* (2013.01); *A61B 5/4547* (2013.01); *G01N 21/359* (2013.01); *G01N 2021/558* (2013.01)

(58) Field of Classification Search
CPC .......... G01N 21/35; G01N 2021/3155; G01N 21/31; G05D 1/0242; H04N 5/33; H04N 3/09; H04N 5/332; A61B 5/441
See application file for complete search history.

(56) References Cited

U.S. PATENT DOCUMENTS 3,961,194 A * 6/1976 Simon et al. .................. 250/334
4,009,392 A * 2/1977 Hanley ....................... 250/338.1
(Continued)

FOREIGN PATENT DOCUMENTS

| JP | 04-301507 A | 10/1992 |
|---|---|---|
| JP | 06221913 | 8/1994 |

(Continued)

OTHER PUBLICATIONS

International Search Report, dated Oct. 18, 2007, PCT/GB2007/050368, Imaging Apparatus and Method, 3 pages.
(Continued)

*Primary Examiner* — Manav Seth
(74) *Attorney, Agent, or Firm* — James M. Stipek; Polsinelli PC

(57) ABSTRACT

Apparatus for inspecting an article comprising: a controller configured to generate a drive signal having a periodic amplitude variation; a source, the source being operable by the controller to emit a source beam thereby to irradiate an article, the source beam comprising a beam of electromagnetic radiation having a periodic amplitude variation corresponding to that of the drive signal; and a detector, the detector being configured to detect a portion of the source beam that has been transmitted through at least a portion of the article, and to generate a detector signal having an amplitude variation corresponding to the amplitude variation of said portion of the source beam, the controller being further configured to generate a difference value corresponding to a difference between the amplitude of the detector signal and the amplitude of a reference signal.

38 Claims, 14 Drawing Sheets

(51) Int. Cl.
*A61B 5/00* (2006.01)
*G01N 21/47* (2006.01)
*G01N 21/55* (2014.01)
*G01N 21/359* (2014.01)

(56) References Cited

U.S. PATENT DOCUMENTS

| | | | | |
|---|---|---|---|---|
| 4,283,629 | A * | 8/1981 | Habermehl et al. | 378/4 |
| 4,317,998 | A * | 3/1982 | Dore | 250/347 |
| 4,321,594 | A * | 3/1982 | Galvin et al. | 340/567 |
| 4,414,833 | A * | 11/1983 | Nicolas et al. | 72/19.1 |
| 4,515,165 | A * | 5/1985 | Carroll | 600/475 |
| 4,914,672 | A * | 4/1990 | Hebrank | 374/124 |
| 4,933,669 | A * | 6/1990 | Lyons | 340/632 |
| 5,101,880 | A * | 4/1992 | Fujiwara et al. | 164/154.4 |
| 5,436,457 | A * | 7/1995 | Tomita | 250/343 |
| 5,477,051 | A | 12/1995 | Tsuchiya | |
| 5,673,746 | A * | 10/1997 | Chun et al. | 164/454 |
| 5,675,070 | A * | 10/1997 | Gelperin | 73/23.34 |
| 6,075,882 | A * | 6/2000 | Mullins et al. | 382/141 |
| 6,085,576 | A * | 7/2000 | Sunshine et al. | 73/29.01 |
| 6,240,309 | B1 | 5/2001 | Yamashita et al. | |
| 6,519,744 | B2 * | 2/2003 | Seidel et al. | 438/7 |
| 6,542,772 | B1 | 4/2003 | Chance | |
| 6,681,635 | B1 | 1/2004 | Van Schaik | |
| 6,753,527 | B1 * | 6/2004 | Yamagishi et al. | 250/339.06 |
| 6,927,857 | B2 * | 8/2005 | Koele et al. | 356/431 |
| 6,996,478 | B2 * | 2/2006 | Sunshine et al. | 702/22 |
| 7,312,454 | B2 * | 12/2007 | Safai et al. | 250/347 |
| 7,627,365 | B2 * | 12/2009 | Chance | 600/475 |
| 7,746,236 | B2 * | 6/2010 | Cole | 340/577 |
| 7,756,305 | B2 * | 7/2010 | Price | 382/128 |
| 7,850,077 | B2 * | 12/2010 | Talwerdi et al. | 235/382 |
| 8,363,887 | B2 * | 1/2013 | Haas et al. | 382/100 |
| 8,759,775 | B2 * | 6/2014 | Forrester | G01N 33/2829 250/339.12 |
| 9,041,923 | B2 * | 5/2015 | Messerchmidt | G01J 3/02 356/301 |
| 2004/0236195 | A1 | 11/2004 | Kawaguchi et al. | |
| 2008/0061238 | A1 * | 3/2008 | Hok | G01N 33/497 250/340 |
| 2008/0191137 | A1 * | 8/2008 | Poteet | G01J 3/02 250/338.1 |
| 2011/0228087 | A1 * | 9/2011 | Hsieh | 348/143 |
| 2013/0200276 | A1 * | 8/2013 | Poteet | G01J 3/02 250/459.1 |

FOREIGN PATENT DOCUMENTS

| | | |
|---|---|---|
| JP | 06-300680 A | 10/1994 |
| JP | 08-285768 A | 11/1996 |
| JP | 2002082097 | 3/2002 |
| JP | 2002519644 | 7/2002 |
| JP | 2003106995 | 4/2003 |
| WO | WO9967649 | 12/1999 |

OTHER PUBLICATIONS

International Preliminary Report on Patentability, dated Jan. 6, 2009, PCT/GB2007/050368, Imaging Apparatus and Method, 9 pages.
Translation of Japanese Patent Publication No. 08-285768, entitled Infrared Scanning Optical System and Inspection Equipment Employing It, 18 pages, Nov. 1, 1996.
Translation of Japanese Patent Publication No. 06-300680, entitled Measuring Apparatus for Interior Quality of Vegetable and Fruit by Transmission Method, 12 pages, Oct. 28, 1994.
Translation of Japanese Patent Publication No. 04-301507, entitled Infrared Type Measuring Apparatus, 1 page, Oct. 26, 1992.
Aug. 12, 1994, English Translation of Patent Abstract with computer translation of Specification, description of prior art, description of drawings and Claims for Japanese patent application No. 04-267046.
Mar. 22, 2002, English Translation of Patent Abstract including computer translated detailed description of invention, description of drawings, and claim(s) of Japanese patent application No. 2000-268816.
Apr. 15, 2012, English Translation of Office action issued in Japanese application 2009-517444 dated Apr. 10, 2012.

* cited by examiner (a)  (b)  (c)

(d)

(a)

(b)

(c)

(d)

(c)

(a)

(b)

IMAGING APPARATUS AND METHOD

FIELD OF THE INVENTION

The present invention relates to imaging apparatus and to a method for investigating an internal structure of an article. In particular, but not exclusively, the invention relates to apparatus and method for imaging concealed objects.

BACKGROUND

Existing technologies such as x-ray imaging systems have been used to investigate the internal structure and properties of a range of objects including food products and the human body. However, systems employing X-rays (or other ionizing radiation) suffer from a range of health and safety concerns. Ionizing radiation is known to be capable of causing damage to tissue and other materials. Consequently, equipment employing x-ray radiation must be provided with sufficient screening to ensure operating and other personnel are not exposed to the radiation.

In addition, the size of an x-ray system is large, and consequently not appropriate in certain manufacturing situations. A further drawback of X-ray systems is the relatively high cost of an X-ray imaging system.

Terahertz imaging systems have also been employed for imaging an internal structure of an article. However, imaging water-containing samples using these systems is challenging due to the high attenuation of terahertz frequency signals by water molecules.

SUMMARY

In a first aspect of the present invention there is provided apparatus for inspecting an article comprising:

a controller configured to generate a drive signal having a periodic amplitude variation;

a source, the source being operable by the controller to emit a source beam thereby to irradiate an article, the source beam comprising a beam of electromagnetic radiation having a periodic amplitude variation corresponding to that of the drive signal; and a detector, the detector being configured to detect a portion of the source beam that has been transmitted through at least a portion of the article, and to generate a detector signal having an amplitude variation corresponding to the amplitude variation of said portion of the source beam, the controller being further configured to generate a difference value corresponding to a difference between the amplitude of the detector signal and the amplitude of a reference signal.

Apparatus according to embodiments of the invention has the advantage that it is capable of providing an image of an internal structure of an article without exposing the article to ionizing radiation. Furthermore, apparatus according to embodiments of the invention does not require ionizing radiation shields or other precautions associated with prior art techniques such as X-ray imaging.

Furthermore, apparatus according to embodiments of the invention has the advantage of being less costly than X-ray imaging systems. Embodiments of the invention have the further advantage that they require less power than X-ray imaging systems and are substantially more portable.

Preferably, the reference signal is a periodic signal having the same frequency as the drive signal. Preferably the amplitude of the reference signal corresponds to the amplitude of the drive signal.

The apparatus may be configured to implement a homodyning function between the reference signal and the detector signal thereby to generate the difference value.

Preferably the reference signal corresponds substantially to the drive signal.

In embodiments of the invention, the detector signal is combined with a reference signal corresponding to the drive signal thereby to generate a signal corresponding to the difference in amplitude between the drive signal and the detector signal.

Preferably the apparatus is configured to implement an autocorrelation function between the reference signal and the detector signal thereby to generate the difference value.

Preferably the apparatus is configured to implement a lock-in detection function between the reference signal and the received signal thereby to generate the difference value.

Use of a reference signal having the same frequency as the drive signal has the advantage that any variations in the frequency of the drive signal are exactly mirrored in the variation of the reference signal. Thus, the difference value may be made substantially independent of variations in the drive signal frequency. Variations in the drive signal frequency may arise for example due to variations in temperature of the electronics associated with the apparatus.

Alternatively or in addition the reference signal may be a periodic reference signal having a frequency different from the drive signal.

The apparatus may be configured to implement a heterodyning function between the reference signal and the detector signal thereby to generate the difference value.

Thus, in embodiments of the invention, the detector signal is combined with a reference signal having a different frequency to the drive signal. In embodiments of the invention the combined signal is passed through a low pass filter arranged to pass a signal of a beat frequency corresponding to the difference between the frequency of the reference signal and the frequency of the detector signal.

Preferably the beam of electromagnetic radiation corresponds to electromagnetic radiation having a wavelength in the range 700 to 2000 nm. This range will also be referred to hereinafter as 'near infrared' or 'NIR' radiation.

This range of wavelength corresponds to a range in which many materials are relatively transparent to electromagnetic radiation. In other words, this range of wavelength corresponds to range in which a sufficient amount of radiation may be transmitted through a sample to enable inspection of an internal structure of the sample to be made in a reasonable length of time.

This range of wavelength also corresponds to wavelengths to which water is relatively transparent to electromagnetic radiation. Thus, imaging of the internal structure of water-containing materials such as biological materials is possible. Thus, apparatus according to embodiments of the invention have the advantage over prior art techniques such as terahertz (THz) imaging techniques that water-containing materials can be imaged. Electromagnetic signals in the THz range of frequencies are strongly absorbed by water, rendering the imaging of the internal structure of biological materials difficult. Whilst THz systems have demonstrated an ability to provide contrast between dry materials, such as between paper without an ink thereon and paper with an ink thereon, they have not been able to demonstrate an ability to provide contrast in biological materials.

Conversely, X-ray imaging systems have demonstrated an ability to provide contrast in biological materials, but have not been able to provide contrast in samples with relatively small concentrations of a different material. For example, X-ray imaging systems are unable to distinguish between paper with an ink thereon and paper without an ink thereon.

The range of frequencies from 700 to about 2000 nm has the advantage that heating of a sample as the electromagnetic radiation passes through the sample does not occur to a significant extent.

Embodiments of the invention have the advantage of being able to distinguish (i.e. provide contrast enabling discrimination between) cysts and tumours in biological materials.

In the case of a cyst, being essentially a water-filled sack, the cyst does not scatter the electromagnetic signal, but rather attenuates the signal. In the case of a tumour or cancer, having a cellular structure on a scale of the order of 1 µm, scattering of the electromagnetic signal occurs. This difference in interaction between the sample and the incident radiation enables more accurate determination of the nature of a feature (such as a cyst or a tumour) in a biological sample to be made. Thus, apparatus according to embodiments of the invention may be used in the detection and characterisation of cysts, tumours and other biological features of a body. The importance of being able to distinguish between cysts and tumours is important in enabling medical practitioners to determine the nature and relative urgency of a medical procedure in respect of a given patient.

Embodiments of the invention are therefore of great potential utility in clinical screening and investigation of patients.

The beam of electromagnetic radiation may correspond to electromagnetic radiation having a wavelength in the range 700 to 1000 nm. In some embodiments the beam of electromagnetic radiation corresponds to electromagnetic radiation having a wavelength in the range 800 to 900 nm.

Preferably the periodic amplitude variation corresponds to a square wave signal.

Alternatively or in addition the periodic amplitude variation may correspond to a sine wave signal.

The apparatus may be operable to move the detector with respect to the article to be inspected.

Alternatively or in addition, the apparatus may be operable to move the article to be inspected with respect to the detector.

This has the advantage that inspection of a plurality of areas of a sample may be performed without the need to provide a corresponding plurality of detectors. Thus, the detector may be moved to an area of the sample where it is desirable to inspect the sample, and a measurement made of a signal transmitted by the source.

In some embodiments of the invention, the relative position of the source with respect to the detector remains substantially unchanged whether the detector is moved with respect to the sample or the sample is moved with respect to the detector.

Preferably the detector comprises a photodetector element.

More preferably, the detector comprises an array of photodetector elements.

This feature has the advantage that parallel collection of data may be performed. In other words, detection of electromagnetic radiation from the source that has interacted with the article to be inspected may be made at a plurality of spatially separate locations at substantially the same time. This has the advantage that it enables data to be collected from a plurality of spatially separate locations more quickly that in the case of serial collection of data. By serial collection of data is meant that data is collected from one spatial location, and subsequently from a second spatial location.

The array may be a linear array. Alternatively the array may be a planar array.

A planar array has the advantage that data may be obtained over a two dimensional area without a requirement to move the detector or the article under inspection.

The apparatus may be configured to operate in a transmission mode whereby the detector is arranged to detect a beam of electromagnetic radiation transmitted through the article to be inspected from one side of the article to the other, the detector being provided on a side of the sample substantially opposite a side wherein the source is provided.

Alternatively or in addition the apparatus may be configured to operate in a reflection mode whereby the detector is arranged to detect a beam of electromagnetic radiation reflected by the article to be inspected, the detector being provided on substantially the same side of the article as the source.

By reflected is included reflection from an outer surface of the article as well as reflection from an inner volume of the article such as an interface between a matrix and an embedded particle. It will be understood by those skilled in the art that the reflection mode of operation therefore includes detection of electromagnetic radiation that has been transmitted through at least a portion of the article under inspection, and is not limited only to detection of electromagnetic radiation reflected from an outer surface of the article.

In a variation of the reflection mode of operation, in some embodiments of the invention one or more reflective elements are provided to reflect electromagnetic radiation transmitted through the specimen back through the specimen to a detector provided on substantially the same side of the specimen as the source.

The apparatus may be configurable to operate in either a reflection mode or a transmission mode.

The apparatus may be configurable to operate in a reflection mode and a transmission mode simultaneously.

The source may be configured to emit electromagnetic radiation of a plurality of wavelengths.

The detector may be configured to detect electromagnetic radiation of a plurality of wavelengths.

A plurality of detectors may be provided, each detector being configured to detect electromagnetic radiation of a different respective wavelength or range of wavelengths.

This feature has the advantage that the apparatus may be used to measure an amount of radiation absorbed by a sample as a function of wavelength of the radiation substantially simultaneously.

The detector may comprise a tunable filter.

This has the advantage that the same detector may be used to measure the amount of radiation incident upon the detector of each of a plurality of wavelengths or range of wavelengths. That is, by performing a plurality of measurements of an amount of electromagnetic radiation detected by the detector, and changing the characteristics of the filter between measurements, the relative amounts of attenuation of a signal by the sample as a function of wavelength may be determined.

At least one of said wavelengths may correspond to a characteristic absorption wavelength of a sample.

This feature has the advantage that analysis of a chemical or other composition of a material may be performed. That is, the apparatus may be used to assist in a determination as to whether a particular material, element or compound is present in an article under inspection.

The source may be a laser source. Laser sources have the advantage that collimation of a beam of radiation from the source is not required. In embodiments of the invention a laser beam in the form of a line is provided, the line being scanned across the sample thereby to obtain an image of a cross-sectional area of the sample, in a similar manner to laser barcode scanning technology.

In some embodiments of the invention a single source such as an LED or solid state laser is employed, in combination with a cylindrical lens in order to generate a linear beam with a relatively flat intensity distribution. In other words, the intensity distribution is substantially non-Gaussian.

At least one of the source and the detector may comprise a fibre optic cable.

The source may be provided with a fibre optic cable, the cable being arranged to direct the beam of electromagnetic radiation onto the article to be inspected.

Alternatively or in addition the detector may be provided with a fibre optic cable arranged to direct electromagnetic radiation from the sample onto the detector.

In a second aspect of the invention there is provided a method of inspecting an article comprising the steps of:

generating a drive signal having a periodic amplitude variation;

generating a source beam of electromagnetic radiation having a periodic amplitude variation corresponding to that of the drive signal;

passing a portion of the source beam through at least a portion of an article to be inspected and to a detector;

generating a detector signal having an amplitude variation corresponding to the amplitude variation of the portion of the source beam passed to the detector; and generating a difference value corresponding to a difference between the amplitude of the detector signal and the amplitude of a reference signal.

Preferably the source beam corresponds to electromagnetic radiation having a wavelength in the range 700 to 2000 nm.

More preferably, the source beam corresponds to electromagnetic radiation having a wavelength in the range 700 to 1000 nm.

Embodiments of the invention will now be described with reference to the accompanying figures in which:

DETAILED DESCRIPTION

Figure 1:
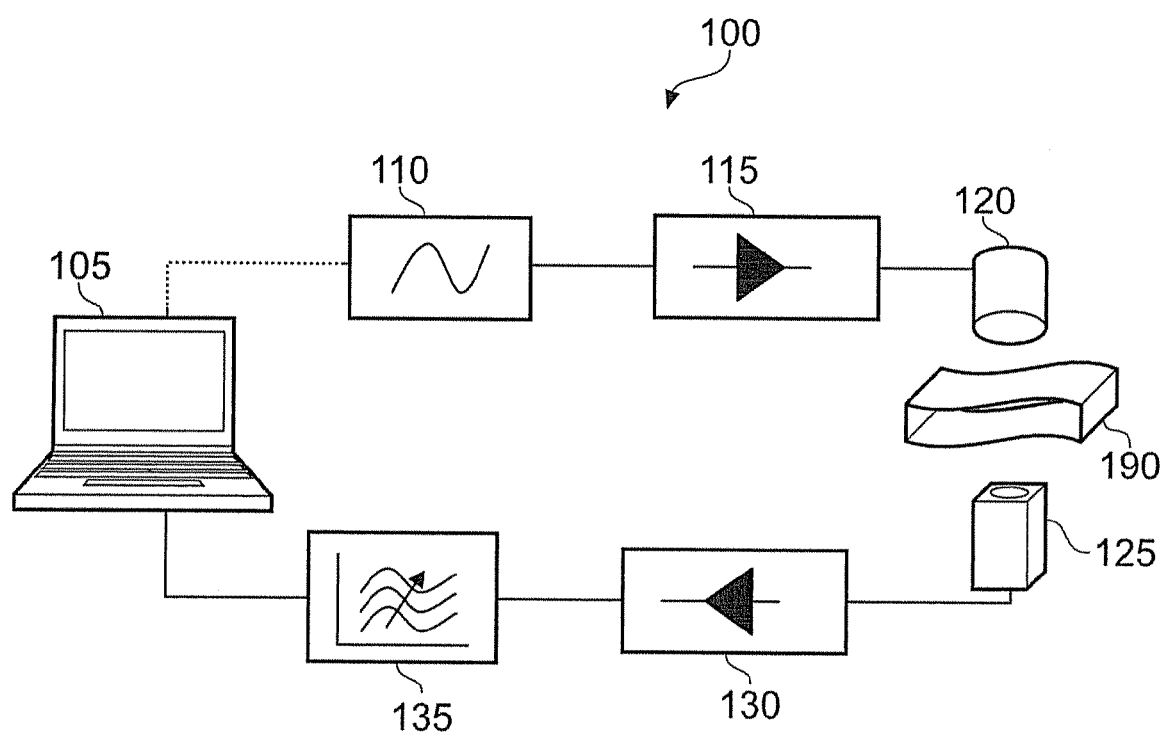
FIG. 1 shows a schematic illustration of apparatus according to a first embodiment of the invention.

According to a first embodiment of the invention, apparatus 100 for inspecting a sample is substantially as shown schematically in FIG. 1. The apparatus is configured to operate in a homodyne mode. In other words, the drive signal and the reference signal are provide by the same signal generator.

The apparatus 100 comprises a computing device 105, a reference (drive) signal generator 110, a reference (drive) signal amplifier 115, a radiation source 120, a radiation detector 125, a detector signal amplifier and conditioner 130 and a signal processing module 135.

The reference signal generator 110 is configured to generate a periodic square wave having a frequency of 10 MHz. It will be appreciated that other frequencies are also useful. In some embodiments the square wave has a periodic frequency of between 1 MHz and 500 MHz.

In some embodiments of the invention the computing device 105 is configured to generate the reference signal instead of a separate reference signal generator 110.

The radiation source 120 according to the first embodiment is a solid state light emitting diode (LED) device configured to emit electromagnetic radiation with a wavelength of around 900 nm. Other wavelengths are also useful.

The radiation detector 125 is a solid state detector having a two dimensional array of detector elements. According to the first embodiment the detector elements are solid state diodes.

Other detector elements are also useful. In some embodiments the detectors are CMOS detectors. In other embodiments of the invention CCD detectors are used. In some embodiments of the invention, any suitable commercially available infra-red camera is used.

In the case that two dimensional arrays of detector elements are used, a lens may be provided to project an image of the sample onto the detector elements.

The detector 125 has an optical bandpass filter arranged to allow only radiation having a wavelength of substantially 900 nm to be incident upon the array of diodes. Bandpass filters corresponding to other wavelengths are also useful.

Variable optical bandpass filters arranged to transmit wavelengths of a different value or range of values are also useful. A diffraction grating is also useful. An adjustable diffraction grating is also useful.

The detector 125 is configured to generate a detector signal corresponding to the amplitude variation of the electromagnetic radiation detected by each of the elements of the detector 125.

The amplifier and conditioner 130 is arranged to process the signal generated by the detector 125 before it is passed to the signal processing module 135.

The amplifier and conditioner 130 performs a precursor function to the signal processing module 135 and is configured to remove extraneous noise.

The amplifier and conditioner 130 is an electrical bandpass filter tuned to the reference signal generated by the reference signal generator 110. The amplifier and conditioner 130 has two main functions.

Firstly, it performs a relatively coarse filtering of the detector signal prior to the main signal recovery process (autocorrelation) performed by the signal processing module 135.

Secondly, the amplifier and conditioner 130 removes harmonics that would otherwise interfere with the autocorrelation performed by the signal processing module.

The signal processing module 135 is provided with a feed of the signal generated by the reference signal generator 110 and a feed of the detector signal following processing by the amplifier and conditioner 130. The signal processing module 135 is configured to perform an autocorrelation of the two signals and to produce an output corresponding to a difference in amplitude of the two signals for each of the elements of the detector 125. In other words, the signal processing module 135 is configured to provide an output that varies in a manner corresponding to variations in the amplitude of the electromagnetic signal passed through a portion of the sample from the source.

Autocorrelation and other lock-in detection techniques have the advantage of enabling substantially noise free data to be obtained. That is, the apparatus is able to filter out of the detector signal frequencies that do not correspond to the reference signal. This enables a more precise comparison of the relative amplitudes of the reference signal and detector signal to be made.

Since the difference in amplitude between the reference signal and the detector signal is small, small signal recovery techniques such as autocorrelation and other lock-in detection techniques provide a valuable means for determining the difference in amplitude between the signals, and thereby recording of a variation in the amplitude of the electromagnetic signal passed through a portion of the sample.

It will be appreciated that the reference signal and the detector signal are signals of the same frequency, and therefore other homodyning techniques are also useful in determining a difference in amplitude of the two signals.

In some embodiments of the invention, heterodyning techniques are used. In some embodiments of the invention a reference signal of a different frequency to the source signal is used.

In some embodiments of the invention, the reference signal is mixed with the detector signal to generate a beat signal. Variations in the amplitude of the beat signal may then be used to measure variations in the amplitude of the detector signal.

In some embodiments of the invention, a reference signal corresponding to harmonic frequencies of the drive signal is used. This enables harmonic analysis to be performed. This enables further information about an article under inspection to be determined.

In some embodiments of the invention employing homodyne techniques the reference (drive) signal is configured to provide a swept frequency signal. That is, the periodic frequency of the reference signal (whether the reference signal corresponds to a square wave signal, a sine wave signal or any other suitable signal) is varied as a function of time. In some embodiments of the invention the reference signal is chirped. Other techniques may also be employed to improve the quality of the comparison of the relative amplitudes of the reference and detector signals.

According to the first embodiment of the invention autocorrelation is performed using single frequency lock-in by means of an analogue circuit. Analogue circuits may be constructed having very high sensitivity to small differences in the amplitudes of the reference and detector signals, enabling high quality images of an internal structure of an article to be obtained.

It will be appreciated that in some embodiments of the invention autocorrelation is performed digitally. Digital performance of autocorrelation has the advantage that it may be performed using a computer running a software program. However it has the disadvantage that analogue to digital (A/D) conversion of the detector signal is required before autocorrelation may be performed. The process of quantization of the detector signal in conversion from an analogue to a digital signal inherently results in a loss of information and therefore a reduction in the quality of data resulting from the autocorrelation process.

In other embodiments of the invention the apparatus is configured to employ other types of small signal recovery techniques including a variety of other lock-in detection techniques. For example, standard multi channel analysers could be employed, or free-running, highly tuned filters that are unconnected and independent of the source. Heterodyning techniques could also be employed as discussed above, or software based signal threshold triggering and averaging techniques used.

Figure 2:
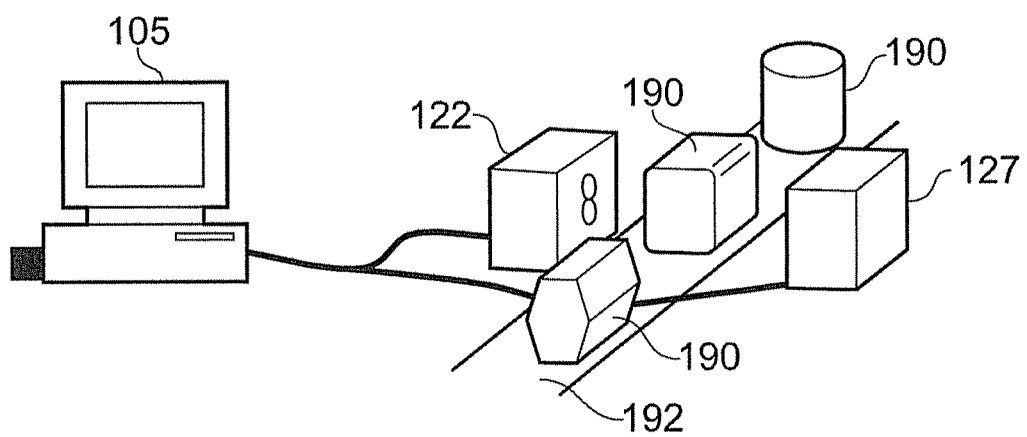
FIG. 2 shows a schematic illustration of apparatus according to the first embodiment of the invention.

FIG. 2 is a schematic diagram of the first embodiment of the invention arranged to analyse articles 190 passing through the apparatus on a conveyor belt 192.

According to the first embodiment the reference signal generator 110, reference signal amplifier 115 and radiation source 120 are provided in a single housing 122. Similarly, the radiation detector 125, radiation detector signal amplifier and conditioner 130 and signal processing module 135 are also provided in a single housing 127.

The apparatus shown in FIG. 1 is arranged to operate in a transmission mode. In other words, the apparatus is configured such that the detector is arranged to detect a beam of electromagnetic radiation transmitted through the article to be inspected. Consequently, the detector 125 is provided on an opposite side of the article to be inspected with respect to the source 120.

In other embodiments of the invention a different arrangement of the relative locations of the source 120 and the detector 125 may be envisaged.

Figure 3:
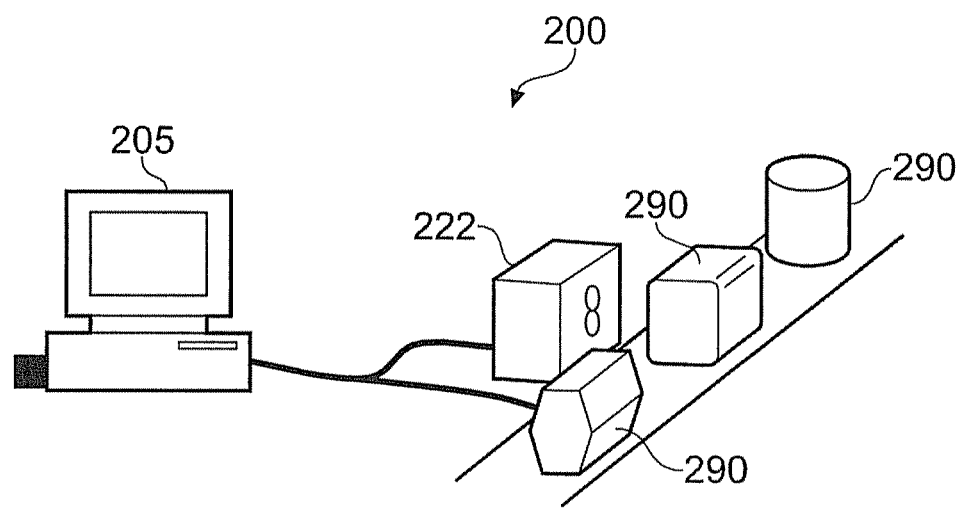
FIG. 3 shows a schematic illustration of apparatus according to a second embodiment of the invention.

In apparatus 200 according to a second embodiment of the invention, the apparatus is arranged to operate in a reflection mode (FIG. 3). In other words, the apparatus is configured such that the detector is arranged to detect a beam of electromagnetic radiation reflected from the article to be inspected.

Thus, the reference signal generator, reference signal amplifier, radiation source, radiation detector, radiation detector signal amplifier and conditioner, and the signal processing module may be provided in a single housing 222. The source and detector are arranged to be located on the same side of the article 290 that is to be inspected with respect to each other.

It will be appreciated that in some embodiments, detectors are provided at locations on both sides of a sample to be inspected, allowing either or both of a transmission mode or a reflection mode of operation to be performed.

Figure 4:
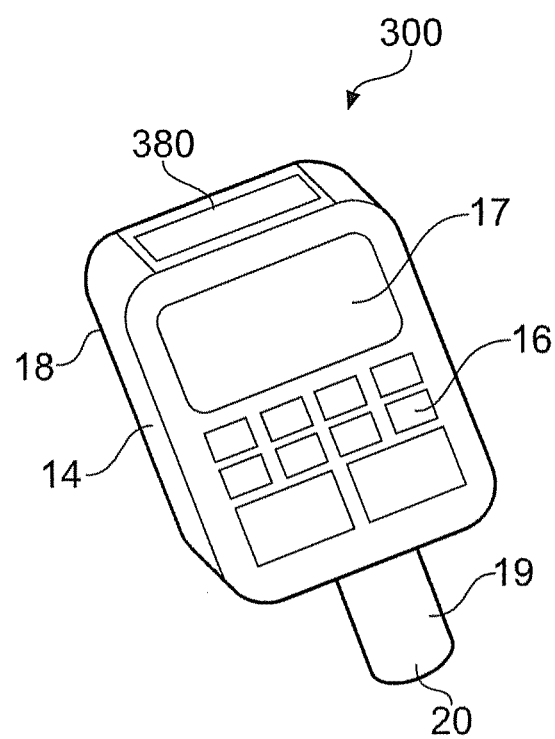
FIG. 4 shows a schematic illustration of apparatus according to a third embodiment of the invention.

Apparatus 300 according to the third embodiment of the invention (FIG. 4) is in the form of a handheld device. The apparatus 300 is arranged to allow a sample to be inserted into a sample chamber 380. Inspection of a sample in the chamber 380 is performed in substantially the same manner as in the case of the first embodiment of the invention. In some embodiments in the form of a handheld device the device is configured to operate in a reflection mode.

Figures 5A, 5B:
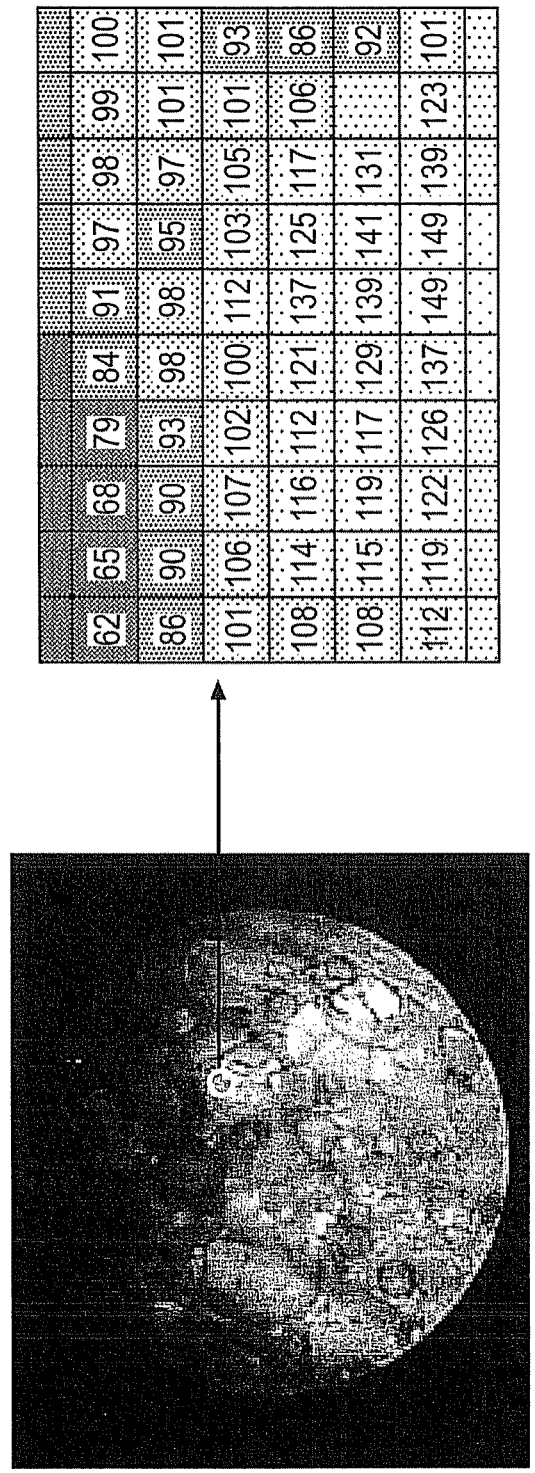
FIG. 5 shows (a) an image obtained from a sample using apparatus according to an embodiment of the invention and (b) pixel values corresponding to an area of the image.

FIG. 5 (a) shows an image of a portion of a food sample obtained by means of apparatus according to the first embodiment of the invention. FIG. 5(b) is a schematic illustration of a portion of an array of pixels of the image corresponding to the area circled in FIG. 5(a). Each pixel corresponds to a detector element of the detector 125. Overlaid on each pixel is a number corresponding to the amplitude of the signal generated by the detector element corresponding to that pixel.

Figures 6A, 6B:
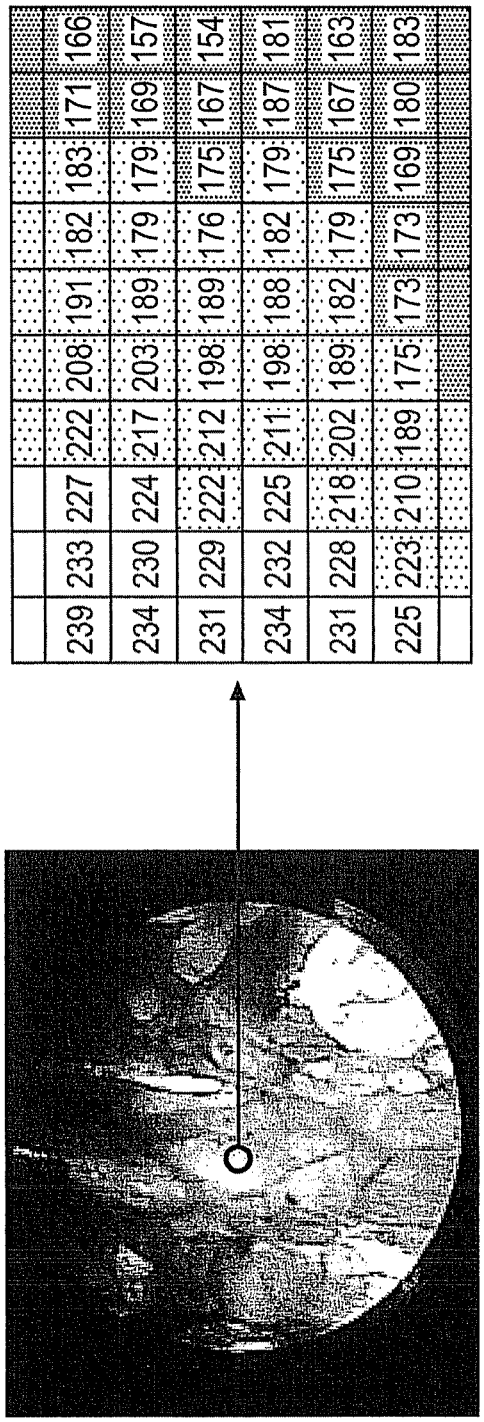
FIG. 6 shows (a) an image obtained from a different sample using apparatus according to an embodiment of the invention and (b) pixel values corresponding to an area of the image.

FIG. 6 (a) shows an image obtained by the same apparatus of a portion of a porous food sample. It can be seen from FIG.

6(b) that the values of amplitude of the signals generated by the detector elements are generally higher than those generated in the case of the more dense sample of FIG. 5. This is because in the case of a more porous sample, a smaller volume of food material constitutes the food sample thereby reducing a volume of food with which the radiation signal can interact, for a given thickness of sample.

Figure 7:
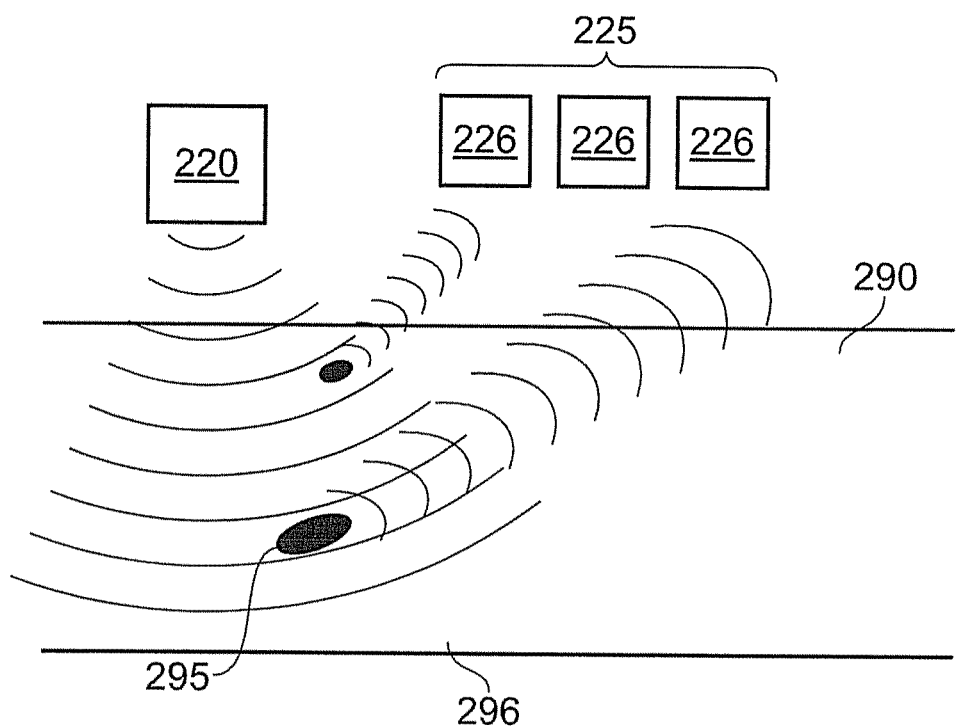
FIG. 7 is a schematic illustration of a reflection mode of operation of apparatus according to the second embodiment.

Embodiments of the invention operating in a reflection mode or a variation of the reflection mode such as that described hereinbefore may be configured according to the arrangement shown schematically in FIG. 7. In the embodiment of FIG. 7, it can be seen that the reflective path length of a beam generated by the source 220 is employed to determine the position of particles 295 embedded in a matrix 296 of a sample 290 under inspection.

The apparatus of FIG. 7 is configured to determine a path length of the reflected beam using a detector 225 having an array of detector elements 226 spatially separated with respect to one another.

Apparatus according to embodiments of the present invention does not use a time-resolved technique in order to determine spatial position of the particles. Rather, embodiments of the present invention are configured to determine an amplitude variation of the source signal passed through a portion of a sample. The amplitude of the source signal decreases as the path length of the signal through the article increases.

However, it will be appreciated by those skilled in the art that time-resolved techniques may also be used in some embodiments of the invention.

Apparatus according to embodiments of the invention may be used to inspect a wide range of materials samples including organic and inorganic materials such as glass, plastic, wood, living and dead tissue, living and dead organisms, and biological materials.

Applications include detection of foreign bodies in articles such as food items. Properties of articles can also be inspected, such as porosity, and density changes variations within a sample may be characterised. Determination of the quality of an article can also be made, for example of food items such as snacks and other items including crisps, cereal bars, biscuits and breads.

Inspection of body parts can also be performed. In some embodiments the apparatus is configured to measure bone size, and provide images of one or more bones of a body. Inspection of bone fractures is also possible, the quality of images obtained using embodiments of the invention being comparable with x-ray imaging techniques. For example, fractures in areas such as fingers, arms, knees, legs, the chest, heels etc may be inspected.

In a factory environment, packaged goods may be inspected to determine characteristics of a packaged food such as a quantity of food contained in a package, fill height, food quality, and whether or not one or more contaminants of a given type are present.

Example 1

Figure 8:
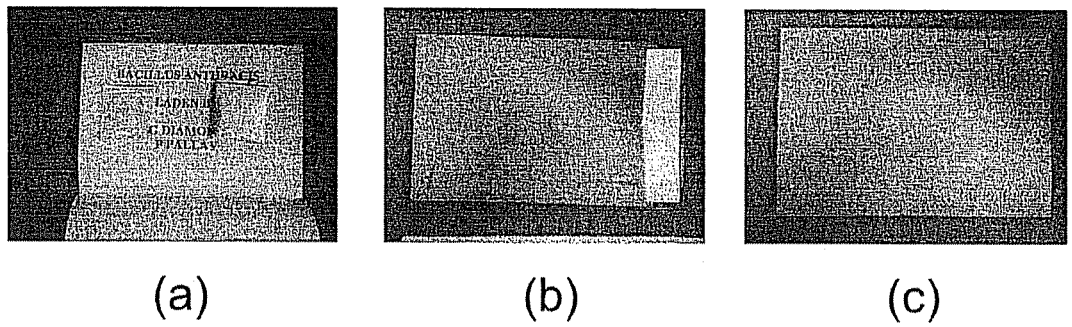
FIG. 8 shows a series of images corresponding to a first example.
Figure 8:
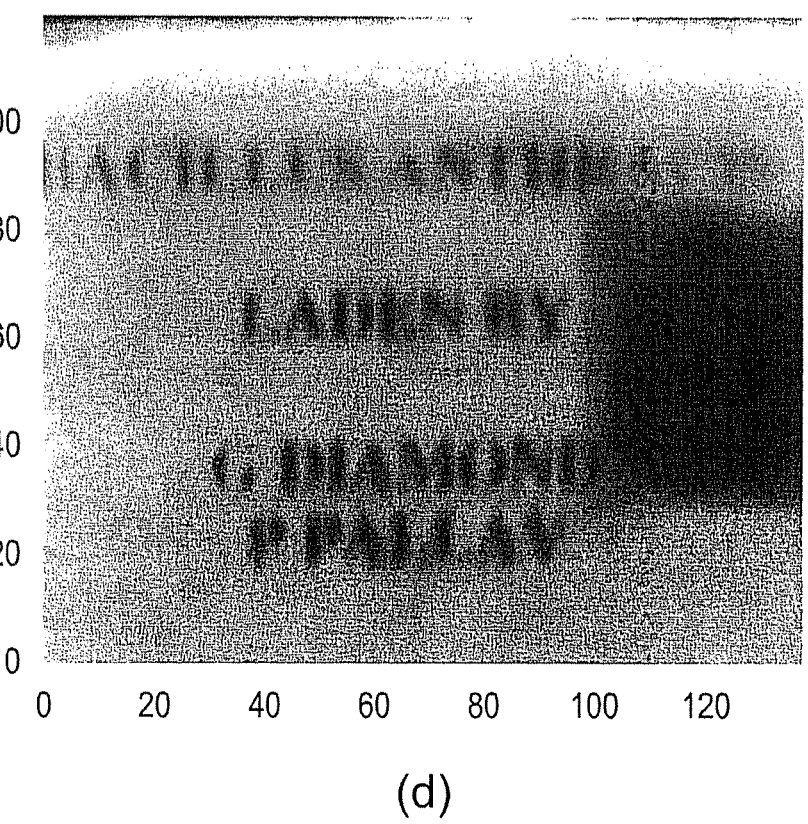

FIG. 8(a) shows a portion of a sample to be inspected in the form of a sheet of paper having text printed thereon. Two bags made of a plastics material and containing a substance in powder form are overlaid on the paper. FIG. 8(b) shows the sheet of paper folded once, during a process of insertion into an envelope. FIG. 8(c) shows the envelope after sealing.

FIG. 8(d) is an image of the sample of FIG. 8(c) obtained using apparatus according to the first embodiment of the invention. Despite the fact that the paper is sealed inside an envelope opaque to visible light, the lettering on the paper is clearly visible and readable in the image.

In apparatus according to embodiments of the invention, the image produced is subsequently processed using further image processing technology such as optical character recognition (OCR) in order to enter the text into a database.

Embodiments of the invention find a wide range of applications relating to security of persons and property. For example, embodiments of the invention may be utilised in mailrooms where scanning of mail passing through the mailroom may be performed.

Scanning of the mail may involve searching for keywords associated with activities of concern to an organisation, such as the words 'bomb' or 'anthrax' etc.

Apparatus according to embodiments of the invention may be associated with existing systems configured to scan mail for address and sort code information.

Apparatus according to embodiments of the invention may be used to identify the presence of chemical substances such as illegal drugs and other prohibited articles such as firearms, in packages such as envelopes, handbags or suitcases, or being carried on or in the human or animal body.

Example 2

Figure 9:
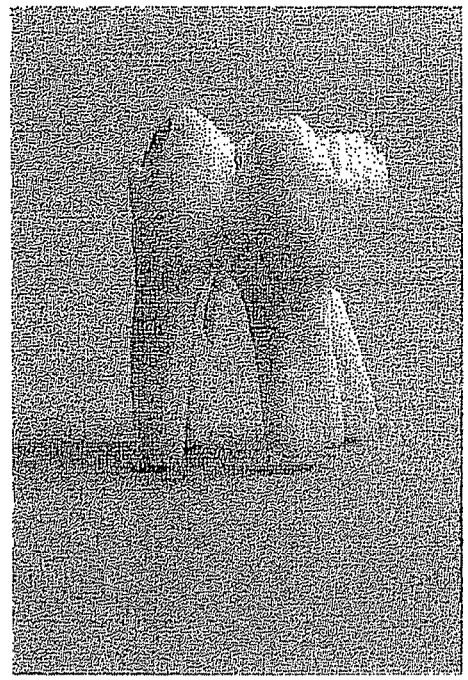
FIG. 9 shows a series of images corresponding to a second example.
Figure 9:
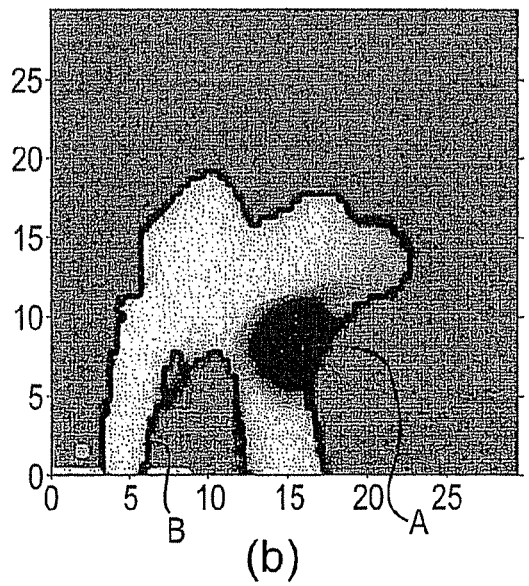
Figure 9:
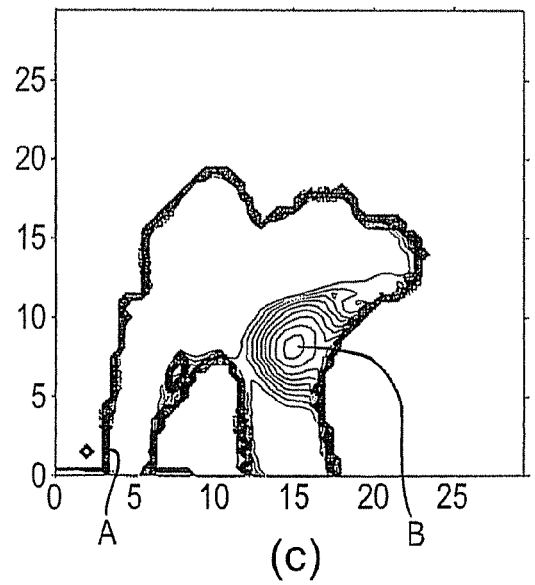
Figure 9:
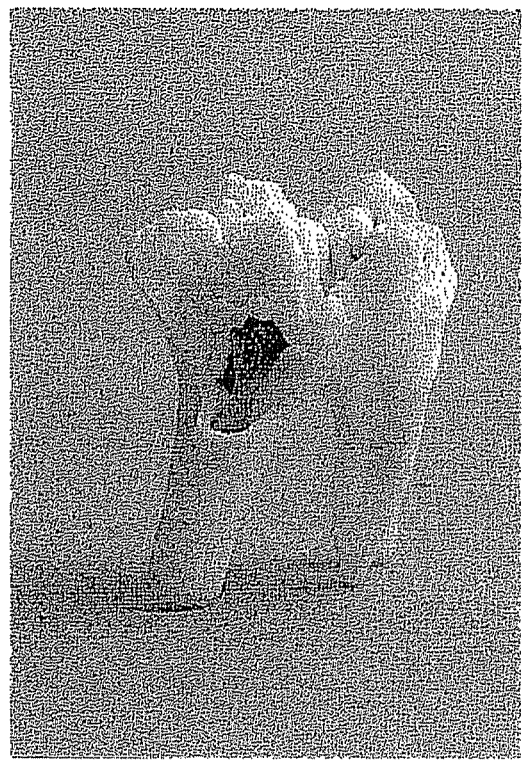

FIG. 9(a) shows a tooth prior to imaging using apparatus according to the first embodiment of the invention. FIG. 9(b) shows a lock-in near infrared (NIR) image of the same specimen taken from the same direction of view as the photograph of FIG. 9(a). FIG. 9(c) shows a corresponding contour plot generated from the data of FIG. 9(b).

A region A of relatively high contrast to the surrounding portions of the tooth is apparent in the NIR images. This area corresponds to a relatively low difference between the amplitudes of the reference signal and detector signal. This indicates that the area A corresponds to a region of relatively low density. It can also be seen that a boundary B between enamel and dentine of the tooth appears relatively dark also. The boundary region is also known to be a region of relatively low density.

FIG. 9(d) is a photograph showing a cut-away portion of the tooth of FIG. 9(a). It can be seen that a cavity exists in the tooth. The position of the cavity corresponds to the position of the region of relatively low density of the tooth as revealed in FIGS. 9(b) and (c).

Example 3

Figure 10:
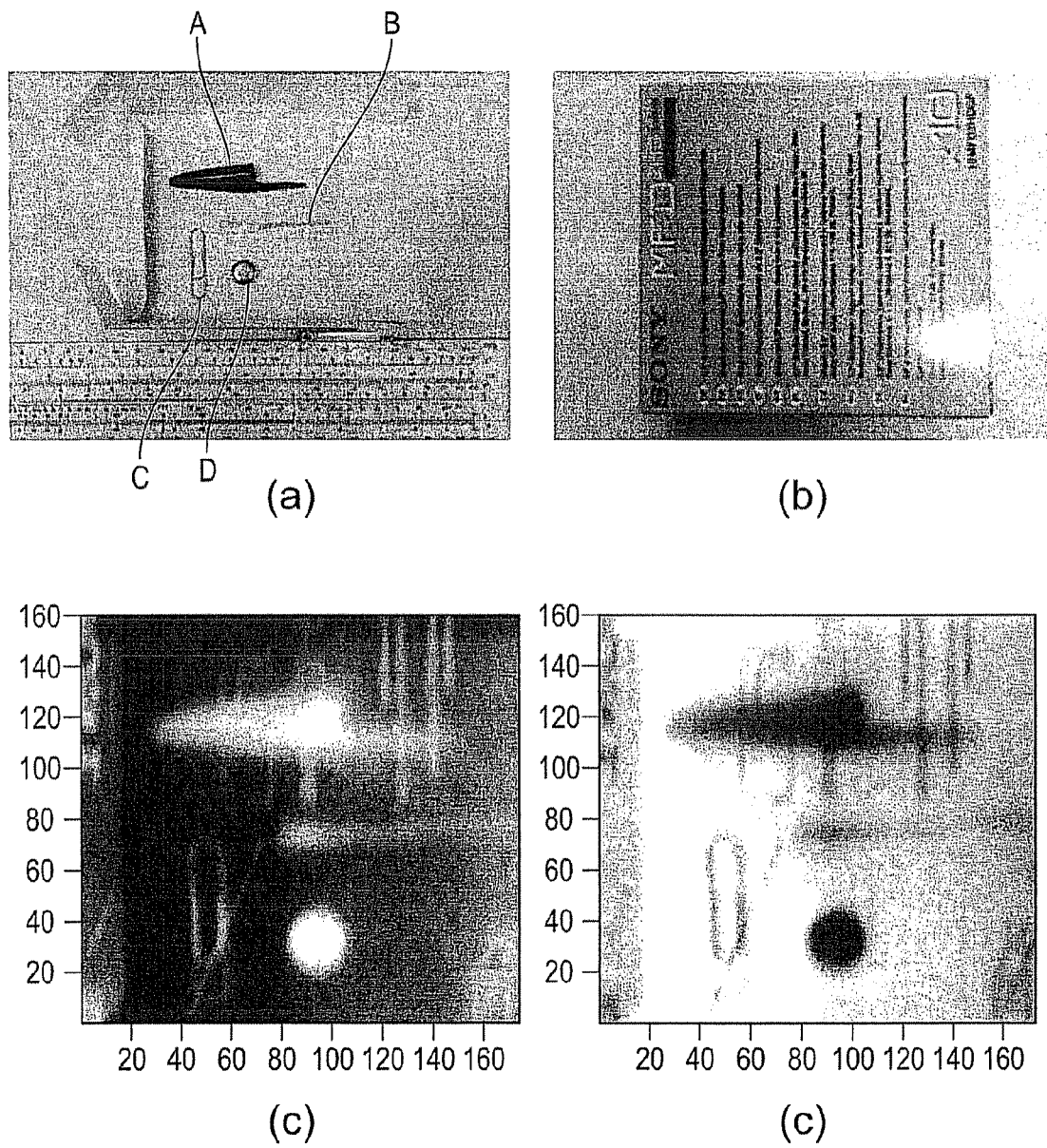
FIG. 10 shows a series of images corresponding to a third example.

FIG. 10(a) is a photograph of four articles (pen lid A, cotton swab on a wooden stick B, paper clip C and watch battery D) made of a range of materials including either metal, plastics, cotton and wood. The articles are shown prior to packaging inside a cardboard box shown in FIG. 10(b).

FIG. 10(c) is a NIR image of the articles using apparatus according to the first embodiment of the invention. FIG. 10(d) shows the image of FIG. 10(c) with reverse contrast. The articles are clearly visible in the images of FIG. 10(c), (d).

It can be seen that NIR imaging is capable of imaging materials that are normally radiolucent to x-rays (such as plastics, wood and cotton) in addition to metals.

The image of FIG. 10(c) was obtained using a NIR source generating near infrared radiation of less than 1 mW of power.

Example 4

Figure 11:
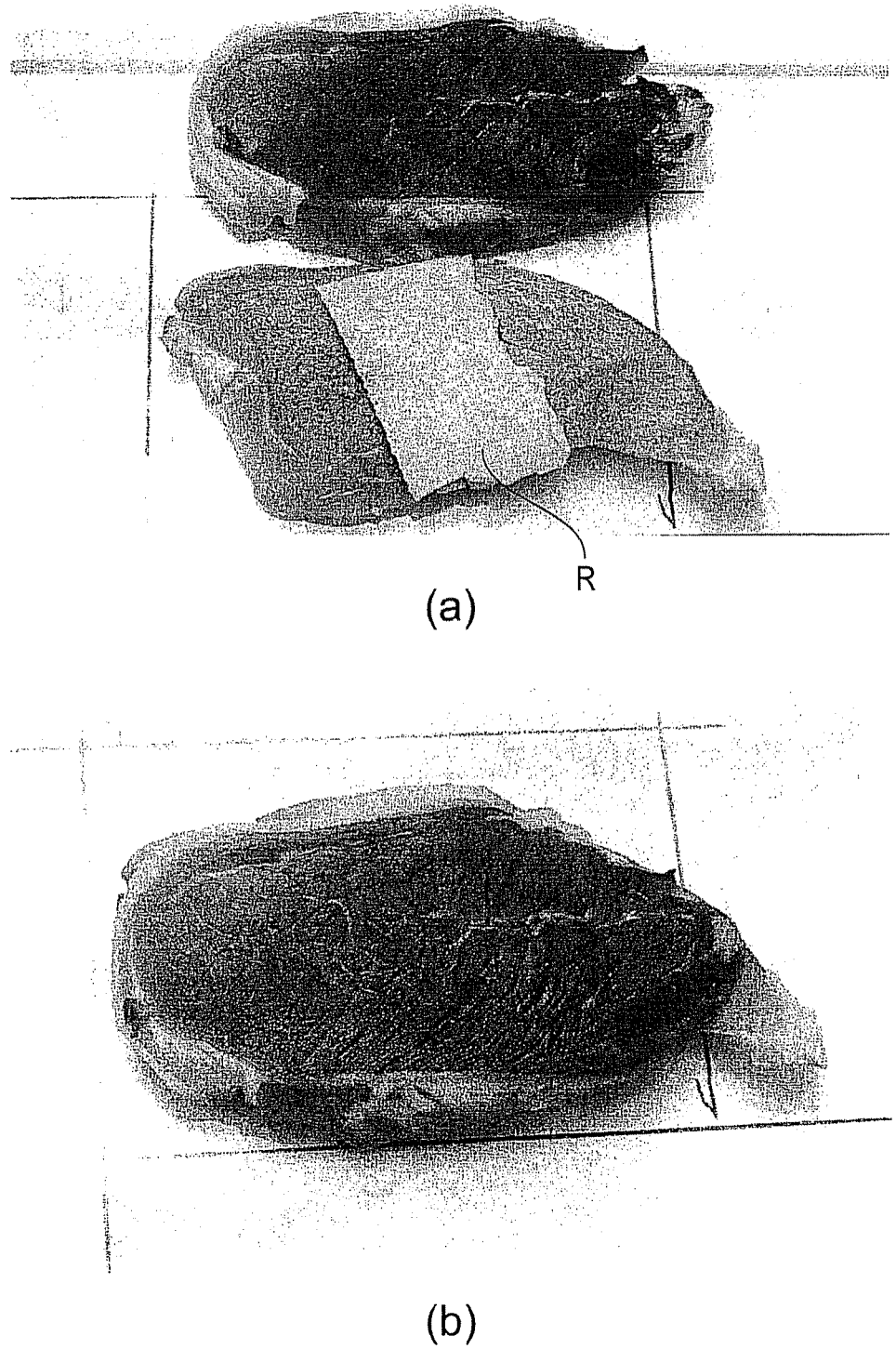
FIG. 11 shows a series of images corresponding to a fourth example.
Figure 11:
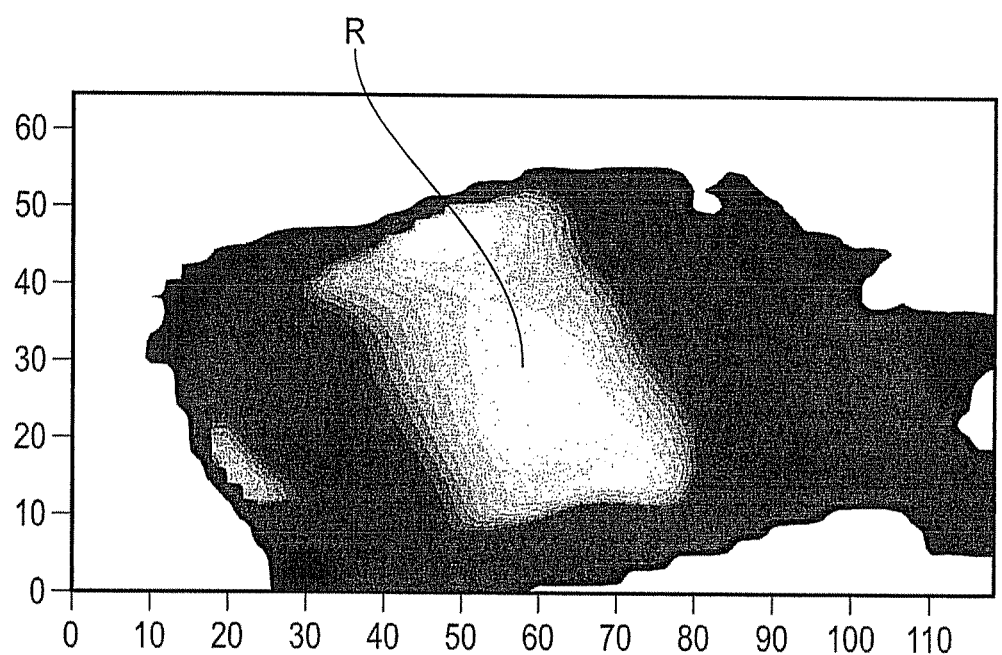

FIG. 11 (a) is a photograph showing two pieces of lean meat (pork) with a section of pork rind R overlaid on one of the pieces (the lower piece) shown in the photograph.

FIG. 11 (b) is a photograph taken with the upper piece of pork overlying the lower piece. The pork rind is thereby 'sandwiched' between the two pieces of meat.

FIG. 11 (c) is a lock-in NIR image of the structure shown in FIG. 11 (b). The presence of the pork rind can be clearly seen in the image. The region in which the rind is located is revealed as a region of relatively large difference in amplitude between the reference signal and the detector signal. The pork rind, being of a relatively high fat content, contains a larger proportion of water which attenuates the NIR signal to a greater extent than portions of the sample having a relatively low fat content.

Also apparent in the image are variations in the structure of the pork rind itself. Furthermore, portions of the pork sample that are thinner than other portions also show a variation in contrast compared with the remainder of the pork sample, such as region 'P' of FIG. 11 (c).

Example 5

Figure 12:
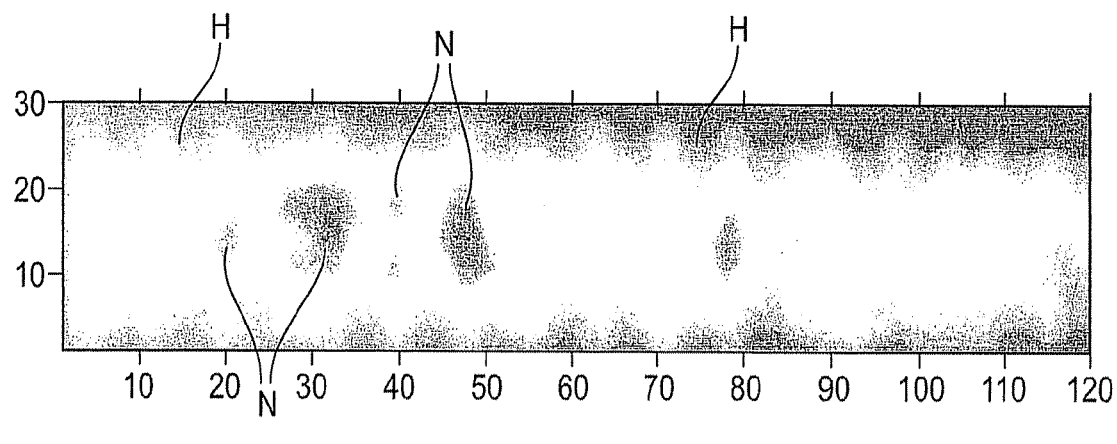
FIG. 12 shows a series of images corresponding to a fifth example.
Figure 12:
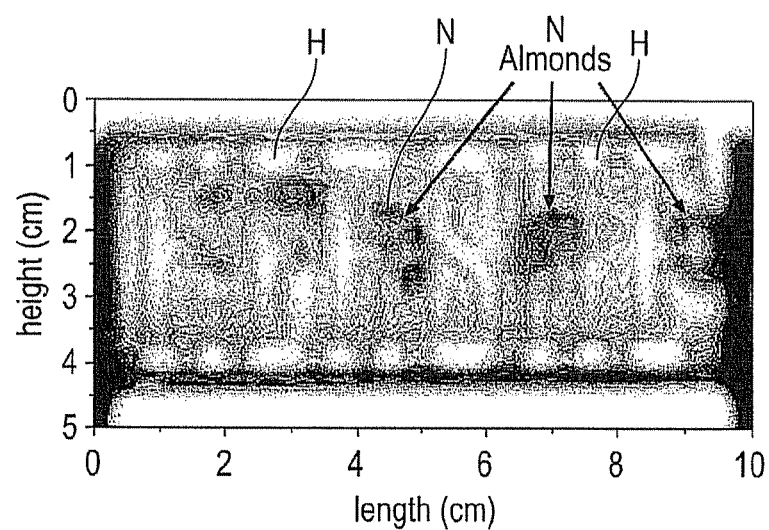

FIG. 12(a) shows a NIR image of a chocolate bar made by the Hershey™ Company. The bar has a thickness variation corresponding to the word "HERSHEY'S". The bar also contains almond nuts embedded within the bar.

Apparatus according to the first embodiment is sufficiently sensitive to distinguish the thickness variations of the bar corresponding to the word "HERSHEY'S". The letters show up as dark lettering on a bright background in the image. The letters "H" are labelled in FIG. 12(a) as a guide to the eye.

The almond nuts embedded in the bars are also clearly visible in the image. The nuts are labelled "N" in FIG. 12(a).

By way of comparison, FIG. 12(b) shows an image of a similar Hershey chocolate bar obtained using a THz imaging system. The system includes a femtosecond pulsed laser Terahertz source and supercooled detector.

The presence of almonds within the chocolate bar, together with the letters "HERSHE" are discernible in the image of FIG. 12(b). The letters "H" are labelled in FIG. 12(b) as a guide to the eye, and nuts are labelled "N".

It is noted that apparatus according to the first embodiment of the invention is approximately three orders of magnitude lower in cost than the THz imaging system used to obtain the image of FIG. 12(b). Furthermore, apparatus according to the first embodiment is several hundred times smaller and substantially less costly to maintain.

Some embodiments of the invention have the advantage that optical elements such as lenses are not required. This has the advantage of reducing a cost of constructing a system according to some embodiments.

In apparatus according to some embodiments of the invention, the source is arranged to emit NIR radiation of a plurality of wavelengths. The source is similarly arranged to detect NIR radiation of a plurality of wavelengths and to measure an intensity of radiation of a given wavelength or range of wavelengths.

Apparatus according to some embodiments is provided with electronically configurable filter elements. The electronically configurable filter elements are arranged to allow a user to control a wavelength of radiation permitted to pass into the detectors of the apparatus.

In some embodiments of the invention a source configured to emit a range of wavelengths of NIR radiation is employed.

In embodiments of the invention the system is configured to record the amplitude of a signal detected by the detector as a function of wavelength by varying the wavelength of radiation passed by one or more filter elements associated with the detector. In some embodiments one or more filter elements are associated with the source instead of or in addition to the detector.

In some embodiments, a plurality of detectors having different respective filters are provided, to enable simultaneous or near-simultaneous detection of different wavelengths of NIR radiation. In such embodiments, a source configured to emit radiation of a plurality of wavelengths or a range of wavelengths is used. Such embodiments have the advantage of enabling more rapid imaging of an article. Rapid imaging of an article can be particularly important when analysing articles travelling at speed along a conveyor belt, or when imaging living objects.

In some embodiments of the invention the source is configured to scan a beam over a portion of a sample. The beam may be in the form of a point, a line, or a broad area beam. A line source may be generated by means of a cylindrical lens and the line scanned over a portion of a sample.

It will be appreciated that embodiments of the present invention may be used at modulation frequencies considerably lower than those used in time of flight analysis systems.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

We claim:

1. Apparatus for imaging an object concealed in an article comprising:
    a controller configured to generate a drive signal having a periodic amplitude variation;
    a source, the source being operable by the controller to emit a source beam thereby to irradiate an article, the source beam comprising a beam of non-ionising electromagnetic radiation having a periodic amplitude variation corresponding to that of the drive signal; and
    a detector, the detector being configured to detect a portion of the source beam that has been transmitted through at least a portion of the article, and to generate a detector signal having an amplitude variation corresponding to the periodic amplitude variation of said portion of the source beam,
    the controller being further configured to perform an autocorrelation or other lock-in detector function between a reference signal related to the drive signal and the detector signal to generate a value corresponding to an amplitude of the portion of the source beam that has been transmitted through at least the portion of the article to image the object concealed in the article in the path of the source beam solely from the amplitudes of the detector signals.

2. Apparatus as claimed in claim 1 wherein the reference signal is a periodic signal having the same frequency as the drive signal.

3. Apparatus as claimed in claim 1 configured to implement a homodyning function between the reference signal and the detector signal thereby to generate the difference value.

4. Apparatus as claimed in claim 1 wherein the reference signal corresponds to the drive signal.

5. Apparatus as claimed in claim 1 wherein the reference signal is a periodic reference signal having a frequency different from the drive signal.

6. Apparatus as claimed in claim 5 configured to implement a heterodyning function between the reference signal and the detector signal thereby to generate the difference value.

7. Apparatus as claimed in claim 1 wherein the beam of electromagnetic radiation corresponds to electromagnetic radiation having a wavelength in the range 700 to 2000 nm.

8. Apparatus as claimed in claim 7 wherein the beam of electromagnetic radiation corresponds to electromagnetic radiation having a wavelength in the range 700 to 1000 nm.

9. Apparatus as claimed in claim 8 wherein the beam of electromagnetic radiation corresponds to electromagnetic radiation having a wavelength in the range 800 to 900 nm.

10. Apparatus as claimed in claim 1 wherein the periodic amplitude variation of the drive signal and the reference signal corresponds to a square wave signal.

11. Apparatus as claimed in claim 1 wherein the periodic amplitude variation of the drive signal and the periodic amplitude variation of the reference signal correspond to a sine wave signal.

12. Apparatus as claimed in claim 1 operable to move the detector with respect to the article to be inspected.

13. Apparatus as claimed in claim 1 operable to move the article to be inspected with respect to the detector.

14. Apparatus as claimed in claim 1 wherein the detector comprises a photodetector element.

15. Apparatus as claimed in claim 1 wherein the detector comprises an array of photodetector elements.

16. Apparatus as claimed in claim 15 wherein the array is a linear array.

17. Apparatus as claimed in claim 15 wherein the array is a planar array.

18. Apparatus as claimed in claim 1 configured to operate in a transmission mode whereby the detector is arranged to detect a beam of electromagnetic radiation transmitted through the article to be inspected, the detector being provided on a side of the article substantially opposite a side wherein the source is provided.

19. Apparatus as claimed in claim 1 configured to operate in a reflection mode whereby the detector is arranged to detect a beam of electromagnetic radiation reflected by the article to be inspected, the detector being provided on substantially the same side of the article as the source.

20. Apparatus as claimed in claim 1 configurable to operate in either a reflection mode or a transmission mode.

21. Apparatus as claimed in claim 1 wherein the source is configured to emit electromagnetic radiation of a plurality of wavelengths or ranges of wavelength.

22. Apparatus as claimed in claim 1 wherein the detector is configured to detect electromagnetic radiation of a plurality of wavelengths or ranges of wavelength.

23. Apparatus as claimed in claim 22 wherein the detector comprises a tunable filter.

24. Apparatus as claimed in claim 22 comprising a plurality of detectors, each of said plurality of detectors being configured to detect a respective different wavelength.

25. Apparatus as claimed in claim 22 wherein at least one of said wavelengths corresponds to a characteristic absorption wavelength of a sample.

26. Apparatus as claimed in claim 1 wherein at least one of the source and the detector comprise a fibre optic cable.

27. Apparatus as claimed in claim 26 wherein the source is provided with a fibre optic cable, the cable being arranged to direct the beam of electromagnetic radiation onto the article to be inspected.

28. Apparatus as claimed in claim 26 wherein the detector is provided with a fibre optic cable arranged to direct electromagnetic radiation from the article onto the detector.

29. Apparatus as claimed in claim 1 wherein the amplitude of the reference signal corresponds to the amplitude of the drive signal.

30. A method of imaging an object concealed in an article comprising:
   generating a drive signal having a periodic amplitude variation;
   generating a source beam of non-ionising electromagnetic radiation having a periodic amplitude variation corresponding to that of the drive signal;
   passing a portion of the source beam through at least a portion of an article to be inspected and to a detector;
   the detector generating a detector signal having an amplitude variation corresponding to the amplitude variation of the portion of the source beam passed to the detector; and
   performing an autocorrelation or other lock-in detector function between a reference signal related to the drive signal and the detector signal to generate a value corresponding to an amplitude of the portion of the source beam that has been transmitted through the at least the portion of the article to image the object therein in the path of the source beam solely from the amplitudes of the detector signals.

31. A method as claimed in claim 30 whereby the source beam corresponds to electromagnetic radiation having a wavelength in the range 700 to 2000 nm.

32. A method as claimed in claim 31 whereby the source beam corresponds to electromagnetic radiation having a wavelength in the range 700 to 1000 nm.

33. Apparatus for imaging an object concealed in an article comprising:
   a controller configured to generate a drive signal having a periodic amplitude variation;
   a source, the source being operable by the controller to emit a source beam thereby to irradiate an article, the source beam comprising a beam of non-ionising electromagnetic radiation having a periodic amplitude variation corresponding to the drive signal; and
   a detector, the detector being configured to detect a portion of the source beam that has been transmitted through at least a portion of the article, and to generate a detector signal having an amplitude variation corresponding to the periodic amplitude variation of said portion of the source beam;
   the controller being further configured to perform an autocorrelation or other lock-in detector function between a reference signal related to the drive signal and the detector signal to generate a value corresponding to an amplitude of the portion of the source beam that has been transmitted through at least the portion of the article to image the object concealed in the article in the path of the source beam solely from the amplitudes of the detector signals, wherein the reference signal is a periodic signal having the same frequency as the drive signal and corresponds to the drive signal, the apparatus being configured to implement a homodyning function between the reference signal and the detector signal thereby to generate the difference value.

34. A method of imaging an object concealed in an article comprising:
generating a drive signal having a periodic amplitude variation;
generating a source beam of non-ionising electromagnetic radiation having a periodic amplitude variation corresponding to the drive signal;
passing a portion of the source beam through at least a portion of the article to be inspected and to a detector;
the detector generating a detector signal having an amplitude variation corresponding to the amplitude variation of the portion of the source beam passed to the detector; and
performing an autocorrelation or other lock-in detector function between a reference final related to the drive signal and the detector signal to generate a value corresponding to an amplitude of the portion of the source beam that has been transmitted through the at least the portion of the article to image the object therein in the path of the source beam solely from the amplitudes of the detector signals by implementing a homodyning function between the reference signal and the detector signal.

35. The method as claimed in claim 30 further comprising generating the source beam of electromagnetic radiation to correspond to electromagnetic radiation having a wavelength in a range 700 to 2000 nm.

36. The method as claimed in claim 30 further comprising detecting, by the detector, a beam of electromagnetic radiation transmitted through the article to be inspected, the detector being provided on a side of the article substantially opposite a side of a source of the source beam.

37. The method as claimed in claim 30 further comprising detecting, by the detector, a beam of electromagnetic radiation reflected by the article to be inspected, the detector being provided on substantially a same side of the article as a source of the source beam.

38. An irradiation and detection apparatus comprising:
a handheld apparatus comprising:
a sample chamber for receiving an article;
a near infrared radiation emitting device for irradiating the article received in the sample chamber and at least one object concealed in the article; and
a near infrared radiation detector arranged to detect infrared radiation to detect the at least one object,
the handheld apparatus configured to operate in a reflection mode.

* * * * *